United States Patent [19]

Stokowksi et al.

[11] Patent Number: 4,988,877
[45] Date of Patent: Jan. 29, 1991

[54] VIA HOLE CHECKER

[75] Inventors: Stanley Stokowksi, Danville; David Wolze, San Jose; Armand P. Neukermans, Palo Alto, all of Calif.

[73] Assignee: Tencor Instruments, Mountain View, Calif.

[21] Appl. No.: 416,764

[22] Filed: Oct. 3, 1989

[51] Int. Cl.⁵ .......................................... G01F 23/00
[52] U.S. Cl. .................................................. 250/358.1
[58] Field of Search ................. 250/358.1, 372.1, 306, 250/307

[56] References Cited

U.S. PATENT DOCUMENTS

| | | | |
|---|---|---|---|
| 4,443,278 | 4/1984 | Zingher | 156/64 |
| 4,578,279 | 3/1986 | Zingher | 427/10 |
| 4,590,376 | 5/1986 | Smith | 250/358.1 |
| 4,680,084 | 7/1987 | Heimann et al. | 156/626 |
| 4,725,332 | 2/1988 | Spohr | 156/626 |

OTHER PUBLICATIONS

S. N. Levine, *Quantum Physics of Electronics*, MacMillan Co., 1965, pp. 150–154.

*Primary Examiner*—Bruce C. Anderson
*Attorney, Agent, or Firm*—Thomas Schneck; John Schipper

[57] ABSTRACT

Method and apparatus for determining the amount, if any, of residue remaining at the bottom of an aperture in a layer of dielectric or insulator material. A layer of electrically conducting material is positioned adjacent to the aperture bottom, an electron collector is positioned adjacent to the mouth of the aperture, and a voltage difference (optional) is impressed between the conducting material and the electron collector. The aperture bottom is illuminated with a light beam with photon energy greater than the electron work function of the conducting material, and a portion of the photons that comprise the light beam reach the conducting material and produce photoelectrons by photoemissive action. A photoelectron current is sensed by the electron collector, and the cleanliness of the aperture bottom is determined from the value of the current.

21 Claims, 1 Drawing Sheet

VIA HOLE CHECKER

TECHNICAL FIELD

This invention relates to determination of the cleanliness of the bottom of a hole or aperture formed in an electrically insulating material.

BACKGROUND OF THE INVENTION

In the semiconductor industry, establishing the integrity of a via hole or aperture, which provides a connection between two separate electrically conducting planes, is a major problem. In the last few years, the size of these via holes or apertures has shrunk substantially, and verifying that the aperture bottom is clean and contains no material that would interfere with flow of charge therethrough has become much more difficult.

As illustrated in FIG. 1, a via aperture 11 is made by etching of a portion of a layer 13 of oxide, nitride or other electrical insulating or dielectric material, where the depth of the aperture may be 0.1-5 $\mu$m and the diameter thereof may be 0.1-5 $\mu$m or even smaller. Because of the high aspect ratio and steep walls of the aperture, it is often difficult to determine when the oxide material is fully penetrated for the first time or whether any residue 15 remains at the aperture bottom. Overetching of the oxide is usually undesirable and can give rise to many other problems. A residue of the oxide or etchant or any other material of thickness of as little as 50 Å can greatly increase the contact resistance, thereby decreasing the reliability of the contact or even eliminating any reasonable conductivity associated with the path defined by the aperture. It is very difficult to inspect or confirm, by any presently known method, the presence of such a residue layer at the aperture bottom. Where an optical method of inspection is used, the small diameter of the hole dictates that only high numerical apertures be used. However, the high aspect ratio of the aperture then produces interference from the dielectric material that surrounds and defines the aperture, and it often becomes impossible to make an accurate reflectance or ellipsometric measurement.

Heimann et al. in U.S. Pat. No. 4,680,084, discloses determining the thickness of an etched semiconductor region by monitoring the intensity of light reflected from the etched layer, where an opaque substrate layer underlies or overlies the etched layer. The opaque layer suppresses the appearance of undesired interference effects in monitoring reflections from the material present in the etched layer and in the layer that would be exposed by a complete etch.

U.S. Pat. No. 4,725,332, issued to Spohr, discloses a method for determining the diameter of one or more microholes formed in a sheet of material. This technique uses a test region that is spaced apart from the fabrication region on the sheet of material. The inventor asserts that, at a porosity of around 0.7 wherein approximately 30 percent of the sheet material remains after formation of see-through holes therein, the electrical and optical characteristics of the remaining material change markedly. Assuming this to be so the technique appears to be limited to determining whether porosity in the sheet, due to appearance of see-through microholes therein, has reached or exceeded 70 percent.

Zingher, in U.S. Pat. Nos. 4,443,278 and 4,578,279, discloses electrical inspection of apertures, and the material left therein, in multilayer ceramic circuits, using techniques such as secondary emission or electrical conductivity measurements on any residue material that remains. The inventor also discloses use of a form of secondary electron emission that uses ultraviolet light as a probe and relies upon some unspecified photoelectric action in the target material (residue). Another method relies upon unspecified use of a light beam and an electron or ion beam in tandem. It is unclear how the Zingher invention would be applied to determining the thickness of dielectric layer residue at the bottom of an aperture.

Thus far, the only reliable method for determination of the presence or absence of any residue at an aperture bottom has been by cleavage of the dielectric material through one of the via apertures and inspection thereof using a scanning electron microscope. This method is very tedious and slow, and this approach interrupts the semiconductor fabrication process. What is needed is a technique for determining the presence or absence of residue at the aperture bottom in a dielectric material, where the technique allows accurate, in-process determination of the interference by such residue with the flow of charge through a channel defined by the aperture. Preferably, the method should also be usable with a variety of dielectric materials and aperture depths and diameters.

SUMMARY OF THE INVENTION

These needs are met by a technique for determining the cleanliness of an aperture bottom formed in a dielectric layer, wherein the dielectric layer overlies a layer of material that may be electrically conducting. The conducting material is assumed to have an electron work function of W(1-6 eV). The aperture bottom is illuminated with a beam of light of a wavelength $\lambda < \lambda_0 = hc/W$, where $h = 6.62 \times 10^{-27}$ erg-sec. is Planck's constant and c is the speed of light. This illumination allows photoelectrons to be liberated in the conducting material that lies beneath the aperture bottom. The fraction of the photoelectrons that pass through any dielectric residual layer lying at the aperture bottom is analyzed to determine the thickness thereof.

BEST MODE FOR CARRYING OUT THE INVENTION

Figure 1:
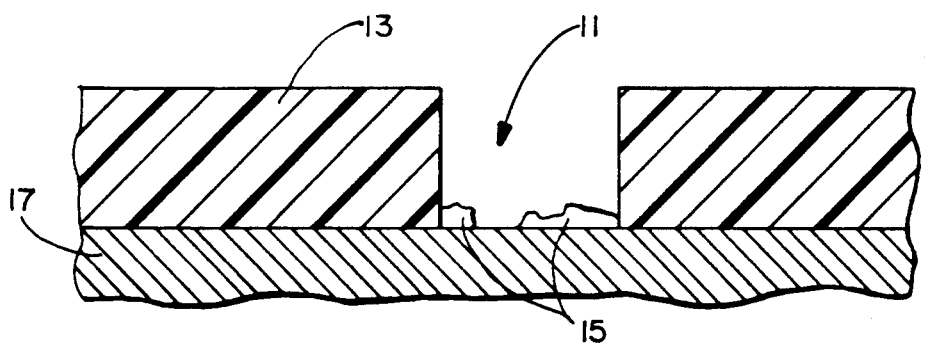
FIG. 1 is a sectional side view of an aperture in a dielectric material, showing a residue covering at least part of the aperture bottom.
Figure 2:
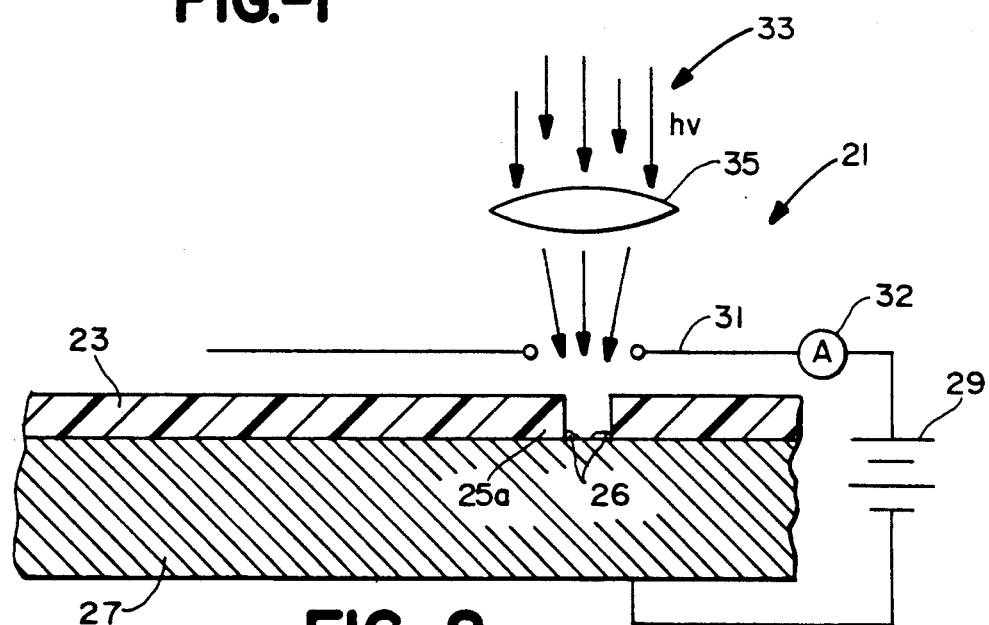
FIG. 2 is a sectional side view illustrating apparatus useful for one technique of determining the presence of a residue at the aperture bottom according to the invention.

With reference to FIG. 2, a system 21 suitable for implementing the invention includes a dielectric layer 23 having one or more apertures 25 formed in the layer 23 so that an unknown amount of residue 26 may remain at the aperture bottom thereof. The residue 26 may be unetched dielectric material, etchant, a product of etching or any other material that would interfere with the flow of charge through the via or channel defined by the aperture 25. The dielectric layer 23 is positioned adjacent to a layer 27 of electrically conducting material such as a semiconductor substrate, and a voltage difference of 5-100 volts is imposed by a bias means 29 (optional) positioned between the electrically conducting layer 27 and an electron collector 31 and associated current measuring device 32 that are adjacent to the mouth of the aperture 25 in the dielectric layer 23. A light source (not shown) provides photons of energy $hc/\lambda$, where $\lambda$ is the wavelength of the photons produced by the light source. For example, each photon of wavelength $\lambda = 0.25$ μm has an associated energy of 4.96 eV. The photons produced by the light source are directed as a beam toward an optical objective 35 that focuses the beam, or a controllable part thereof, on the aperture bottom of an aperture 25. The light source, the electron collector 31, and current measuring device 32 may move from one such aperture to another in a predetermined sequence.

If little or no residue 26 is present at the bottom of the aperture 25, most or all of the photons in the portion of the beam 33 that are focused at the aperture bottom will pass through the residue into the conducting material of the layer 27 that lies directly below the aperture bottom and will produce photoelectrons by the well-known photoemissive action in the conductive layer 27. A portion of the photoelectrons thus liberated within the layer 27 will be transported through the residue 26, if any, present at the aperture bottom of the aperture 25 and will be collected by the electron collector 31 positioned near the mouth of the aperture 25 as shown. Although photoelectrons may also be produced within a portion of the conducting layer 27 that does not lie directly beneath the bottom of an aperture such as 25, these photoelectrons will make little or no contribution to the current collected at the electron collector 31 because such photoelectrons must be transported through a substantial thickness (of the order of 1 μm or more) of the overlying dielectric layer 23. Thus, the photoelectron current collected at the electron collector 31 may be used as a measure of the cleanliness of the residue 26, if any, present at the aperture bottom in the aperture 25. As the residue thickness increases, or the fraction of the aperture bottom covered by the residue increases, the number of photoelectrons produced by such photons in the conducting layer 27 decreases, and the photoelectron current collected by the electron collector 31 also decreases. As a result of this behavior, the absolute or relative number of photoelectrons collected by the collector 31 becomes a very sensitive measure of the amount of residue, if any, present at the bottom of the aperture 25.

Figure 3:
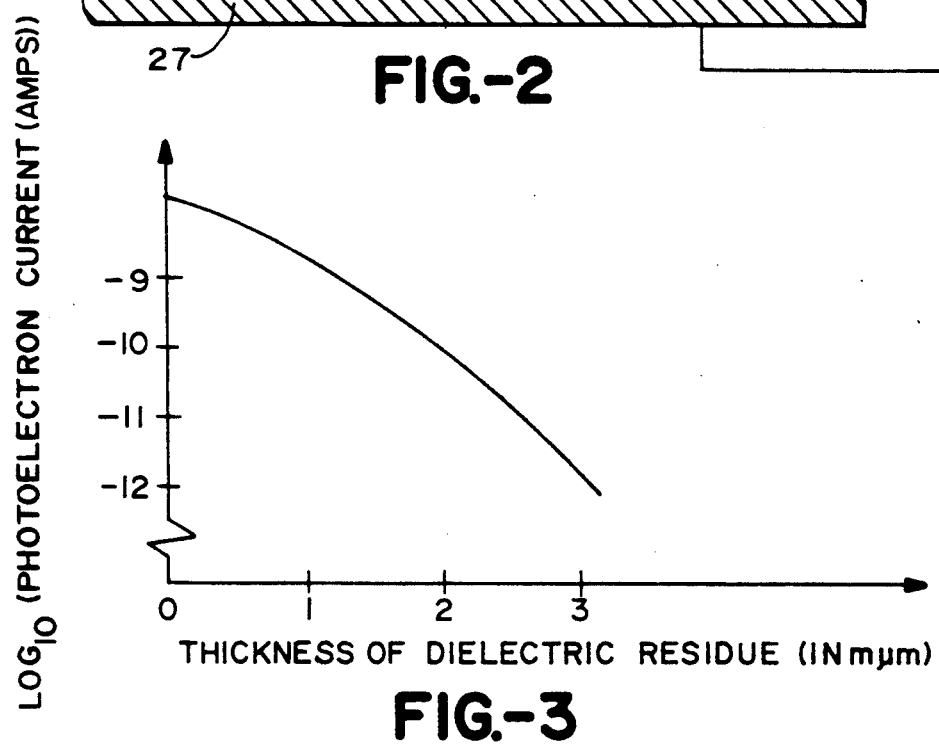
FIG. 3 is a graphical view of photoelectron count sensed at an electron collector as a function of dielectric residue thickness for a representative dielectric such as $SiO_2$ or $Si_3N_4$.

A representative photoelectron count as a function of the thickness of the dielectric residue is shown in FIG. 3. As dielectric residue thickness increases, the corresponding photoelectron current falls precipitously as shown. A suitable range for the thickness of the residue at the aperture bottom is 0–100 Å for many materials. For an overlying thickness of $SiO_2$ of 50 Å, the current collected by the electron collector 31 in FIG. 2 is often of the order of 0.1–10 picoamperes. The curve shown in FIG. 3 is not universal, and the photoelectron current will vary with the particular dielectric material and illumination wavelength used, with the particular electrically conducting material used, with the voltage bias applied between the electron collector 31 and the conducting layer 27 in FIG. 2, and with other parameters.

Photoelectrons can be emitted from electrically conducting materials such as silicon (doped or undoped), germanium, gallium arsenide, polysilicon and metals such as aluminum, tungsten and molybdenum, when the light illuminating such materials is sufficiently energetic. Metal silicides, such as titanium silicide, platinum silicide, palladium silicide, cobalt silicide, zirconium silicide, tantalum silicide, hafnium silicide, niobium silicide, vanadium silicide, nickel silicide, tungsten silicide and molybdenum silicide, are also attractive for the conducting material. These silicides have resistivities of no more than 100 Ohm-cm. Generally, it is required that the photon energy $hc/\lambda$ be greater than the work function W of the conducting material, according to the model proposed and proved by Einstein and discussed briefly in texts such as *Quantum Physics of Electronics* by S.N. Levine, MacMillan Co., 1965, pp. 150-154. However, if the electrically conducting material is covered with a layer of dielectric material or contaminants, the photoelectron current, as sensed at the electron collector, decreases, because the emitted electrons have low energy and are scattered during their transport through the overlying dielectric layer. Preferably, the resistivity of the conducting material should be about $10^6$ Ohm-cm or less.

The aperture bottom of the aperture 25 shown in FIG. 2 is preferably illuminated by light of ultraviolet wavelength ($\lambda < 0.4$ μm) so that the energy of an individual photon is greater than the work function W of the electrically conducting material in the layer 27 by at least 1–2 eV. The light source may be any UV source (coherent or noncoherent) such as deuterium, a low pressure mercury lamp or an excimer laser that utilizes molecular combinations such as ArF, ArCl, KrF, KrCl, XeF, XeCl, Ne+Ne, Ar+Ar, Kr+Kr or Xe+Xe. Preferably, the light beam diameter is made slightly larger than the aperture diameter to allow for some misregistration between the light beam and the aperture bottom. Because of the short wavelengths used here, it is relatively easy to obtain small beam diameters. For example, at a light wavelength of $\lambda = 0.25$ μm, the diffraction limited light beam diameter is also about 0.25 μm with a numerical aperture of NA=0.5, where an excimer laser is used. The peak intensity of light illuminating the aperture bottom should be limited to avoid inducing surface or bulk reactions such as photo-dissociation of the dielectric material.

Although it is difficult to predict a priori the photoelectron current from the electrically conducting material, a small amount of experimentation should suffice to establish a good correspondence between the photoelectron current collected by the electron collector and the extent of the residue at the aperture bottom, for a light source of fixed intensity and wavelength. For example, contact resistance measured between the two conducting planes, after fill-in of the apertures with electrically conducting material, may be used to empirically determine the amount of residue or the fraction of the aperture bottom covered by the residue.

If necessary, more than one aperture can be included in the light beam and the total photoelectron current from all the apertures can be summed to determine an average dielectric residue thickness at the aperture bottoms for the apertures thus illuminated. This will increase the inspected area of the dielectric layer at the bottom of the holes, at the expense of poorer spatial resolution. Additionally, the fraction of light used effectively will decrease because the fill factor or ratio of aperture area to total illuminated area will decrease when the light beam diameter is increased to cover a plurality of adjacent apertures.

Dielectrics such as oxides are at least partly transparent to deep ultraviolet light so that most of the light traveling through the dielectric 23 (FIG. 2) will reach the conducting layer 27 in FIG. 2. Although photoelectrons will be liberated beneath all portions of the dielectric illuminated by the light beam, the escape probability of the photoelectrons will be very low except for those liberated directly below the residue 26 (assumed to be very small) at the aperture bottom.

Free electrons tend to attach themselves to water or oxygen molecules, thereby creating negative ions that tend to impede the flow of charge to the electron collector. It may, therefore, be preferable to provide an atmosphere of inert gases that resist electron attachment in the apertures. Such gases include He, Ne, Ar, Kr, Xe and $N_2$. These gases need be supplied only in the areas adjacent to the apertures themselves so that the gases can be brought into the optical objective 35 shown in FIG. 2.

Alternatively, a vacuum of associated pressure $p = 10^{-1} - 10^5$ Pascals can be established in the apertures to increase the yield of photoelectrons collected at the electron collector. Use of a high vacuum environment in the apertures will allow the use of deep uv light of wavelength $\lambda < 0.18$ $\mu$m, another advantage of provision of a vacuum here. If the ambient atmosphere contains only $N_2$ or some other gas that does not contain oxygen, use of a high vacuum may not be required for illumination with deep uv light.

One recurring problem here is the low photoelectron current (of the order of a few picoamperes or less) collected by the electron detector 31 in FIG. 2 for dielectric residue thicknesses of the order of 50 Å or greater. The signal-to-noise ratio S/N may be improved by increasing the electron collector-substrate voltage, or applying a bias if none is used, so that the electrical field E in the hole, measured from the aperture bottom to the electron detector, is relatively high, say $E = 10^2 - 10^4$ volts/cm. However, this electrical field should not be increased to the point at which the electrical field may cause (1) significant field emission from the adjacent solid material or (2) significant discharge or electron avalanche multiplication of the electrons collected at the detector.

Alternatively, a dc light source may be replaced by a pulsed or modulated light source, with or without synchronous detection, to enhance the signal-to-noise ratio in the detection.

We claim:

1. A method for determining the cleanliness of the bottom of an aperture formed in a layer of dielectric material, the method comprising the steps of:
   providing a layer of electrically conducting material adjacent to a bottom surface of the dielectric layer, where this conducting material is characterized by an electron work function W, said aperture extending downward through said dielectric layer to said layer of conducting material;
   illuminating the aperture and surrounding area from above said dielectric layer with light having a wavelength component that stimulates photoemission in the underlying conducting material, thereby causing photoelectrons to be liberated from the layer of conducting material that lies beneath the aperture and nearby surrounding dielectric layer, a portion of the photoelectrons passing through any dielectric material lying at the bottom of the aperture to produce a photoelectron current, photoelectrons liberated beneath said dielectric layer being scattered by said dielectric layer and contributing little to said photoelectron current; and
   determining the photoelectron current that emerges from the aperture, whereby the cleanliness of the bottom of the aperture is determined.

2. The method of claim 1, wherein said step of determining said photoelectron current comprises the steps of:
   providing an electron collector at a top surface of said dielectric layer adjacent to the mouth of said aperture to collect said photoelectrons; and
   providing a positive voltage difference between the electron collector and said layer of said electrically conducting material.

3. The method of claim 2, wherein said step of providing said positive voltage difference includes providing a voltage in the range of 5–100 volts for said electron collector relative to the voltage of said electrically conducting material.

4. The method of claim 2, wherein said step of providing said positive voltage difference includes providing an electrical field in the range of $10^2 - 10^4$ volts/cm in said aperture, measured from said aperture bottom toward said electron collector.

5. The method of claim 1, wherein said step of providing said layer of said electrically conducting material includes selecting said electrically conducting material from the class of materials with electrical resistivities of no more than $10^6$ Ohm-cm that consists of silicon, germanium, gallium arsenide, polysilicon, tungsten and aluminum, molybdenum, titanium silicide, platinum silicide, palladium silicide, cobalt silicide, zirconium silicide, tantalum silicide, hafnium silicide, niobium silicide, vanadium silicide, nickel silicide, tungsten silicide and molybdenum silicide.

6. The method of claim 1, wherein said step of illuminating said aperture with said light includes providing said light with a light wavelength of at most 0.4 $\mu$m.

7. The method of claim 1, further including the step of providing said light that illuminates said aperture as a light beam with a diameter greater than the diameter of said aperture.

8. The method of claim 1, wherein said dielectric layer has a plurality of said apertures therein, the method further comprising the step of illuminating the aperture of a second aperture in said dielectric layer with said light having a wavelength that stimulates photoemission in said conducting material substantially simultaneously with illumination of said first aperture.

9. The method of claim 1, wherein said dielectric material has a plurality of said apertures therein, the method comprising the step of sequentially illuminating at least two apertures with said light having wavelength that stimulates photoemission in said conducting material.

10. The method of claim 1, further comprising the step of providing in said aperture an atmosphere composed of one or more gases that have a relatively low likelihood of electron attachment thereto.

11. The method of claim 10, wherein the step of providing said atmosphere of one or more of said gases in said aperture includes choosing said gas from the class of relatively inert gases consisting of He, Ne, Ar, Xe, Kr and $N_2$.

12. The method of claim 1, further comprising the step of providing in said aperture an ambient atmosphere of pressure in the range of $0.1–10^5$ Pascals.

13. The method of claim 1, further comprising the step of providing in said aperture an ambient atmosphere of less than 0.1 Pascals.

14. The method of claim 1, wherein said thickness of said dielectric material at said aperture bottom lies in the range 0–100 Å.

15. Apparatus for determining the cleanliness of the bottom of an aperture formed in a layer of dielectric material where the aperture bottom is adjacent to an underlying layer of electrically conducting material with associated work function W, the apparatus comprising:

a light source, to provide a light beam of wavelength $\lambda < \lambda_o = hc/W$, where $h = 6.62 \times 10^{-27}$ erg-sec. and c is the speed of light;

positioning means to position the light source above said aperture so that it illuminates the aperture and nearby surrounding dielectric layer with the light beam; and an electron collector, positioned adjacent to the mouth of the aperture, to collect photoelectrons that emerge from any dielectric layer residue at the aperture bottom and appear as a photoelectron current at the aperture mouth.

16. The apparatus of claim 15, wherein said electron collector comprises:

collection means for collecting and counting said photoelectrons; and bias means for imposing a positive voltage difference in the range of 5–100 volts between the collection means and said layer of electrically conducting material.

17. The apparatus of claim 15, wherein said layer of electrically conducting material has electrical resistivity of no more than $10^6$ Ohm-cm and is drawn from the class consisting of silicon, germanium, gallium arsenide, polysilicon, tungsten and aluminum.

18. The apparatus of claim 17, wherein said light wavelength is at most 0.4 μm.

19. The apparatus of claim 15, further comprising gas means for providing an atmosphere in said aperture of one or more gases that have a relatively low likelihood of electron attachment thereto.

20. The apparatus of claim 19, wherein said gas in said aperture is drawn from the class of relatively inert gases consisting of He, Ne, Ar, Xe, Kr and $N_2$.

21. The apparatus of claim 15, further comprising vacuum means for providing in said aperture a vacuum atmosphere of pressure in the range of $0.1–10^5$ Pascals.

* * * * *

UNITED STATES PATENT AND TRADEMARK OFFICE
CERTIFICATE OF CORRECTION

PATENT NO. : 4,988,877

DATED : January 29, 1991

INVENTOR(S) : Stanley Stokowski et al

It is certified that error appears in the above-identified patent and that said Letters Patent is hereby corrected as shown below:

ON THE TITLE PAGE

Below "United States Patent [19]", "Stokowksi et al." should read --Stokowski et al.--.

In "[75] Inventors:", "Stanley Stokowksi" should read --Stanley Stokowski--.

Signed and Sealed this

Thirtieth Day of June, 1992

Attest:

DOUGLAS B. COMER

Attesting Officer

Acting Commissioner of Patents and Trademarks